United States Patent [19]

Hamblin et al.

[11] Patent Number: 5,547,117
[45] Date of Patent: Aug. 20, 1996

[54] HANDLE ACTUATOR FOR SURGICAL INSTRUMENT HAVING CLAMP LOCK AND EMERGENCY RELEASE

[75] Inventors: Steven W. Hamblin; David A. Witt, both of Loveland; Thomas J. Sierocuk; Kirk M. Nicola, both of West Chester; Matthew R. Otten, Cincinnati; Craig B. Berky, Milford, all of Ohio

[73] Assignee: Ethicon Endo-Surgery, Cincinnati, Ohio

[21] Appl. No.: 484,475

[22] Filed: Jun. 7, 1995

Related U.S. Application Data

[62] Division of Ser. No. 219,846, Mar. 30, 1994, abandoned.

[51] Int. Cl.⁶ ................................................. A61B 17/068
[52] U.S. Cl. .................... 227/175.2; 227/176.1; 227/178.1; 227/19
[58] Field of Search .................... 227/19, 8, 179, 227/176, 175, 175.1, 176.1, 178.1, 175.2

[56] References Cited

U.S. PATENT DOCUMENTS

| | | | |
|---|---|---|---|
| 4,869,414 | 9/1989 | Green et al. | 227/19 |
| 5,307,976 | 5/1994 | Olson et al. | 227/19 |
| 5,332,142 | 7/1994 | Robinson et al. | 227/8 |
| 5,333,773 | 8/1994 | Main et al. | 227/179 |
| 5,452,836 | 9/1995 | Huitema et al. | |
| 5,465,894 | 11/1995 | Clark et al. | 227/19 |
| 5,465,895 | 11/1995 | Knodel et al. | 227/19 |

FOREIGN PATENT DOCUMENTS

| | | |
|---|---|---|
| 0216532A1 | 4/1987 | European Pat. Off. |
| 0593920A1 | 4/1994 | European Pat. Off. |
| 0600182A2 | 6/1994 | European Pat. Off. |
| 0603472A2 | 6/1994 | European Pat. Off. |
| 0674876A3 | 4/1995 | European Pat. Off. |
| WO8602256 | 4/1986 | WIPO |

Primary Examiner—Scott A. Smith
Attorney, Agent, or Firm—Michael J. Kline; Paul Coletti; Matthew Goodwin

[57] ABSTRACT

A surgical stapling instrument with a remotely articulated staple head assembly on a rotatable support shaft. A joy stick mounted to the shaft of the instrument near the handle allows for remote articulation of the staple head assembly. The staple head assembly includes a narrow contour for insertion between adjacent rib pairs without rib spreading. The staple head assembly further includes a reloadable staple cartridge which may be replaced with differently sized staples of a second cartridge. A closure trigger clamps tissue prior to stapling and cooperates with a second trigger that performs the staple firing operation. The triggers include a safety lock mechanism for preventing premature staple firing.

9 Claims, 10 Drawing Sheets

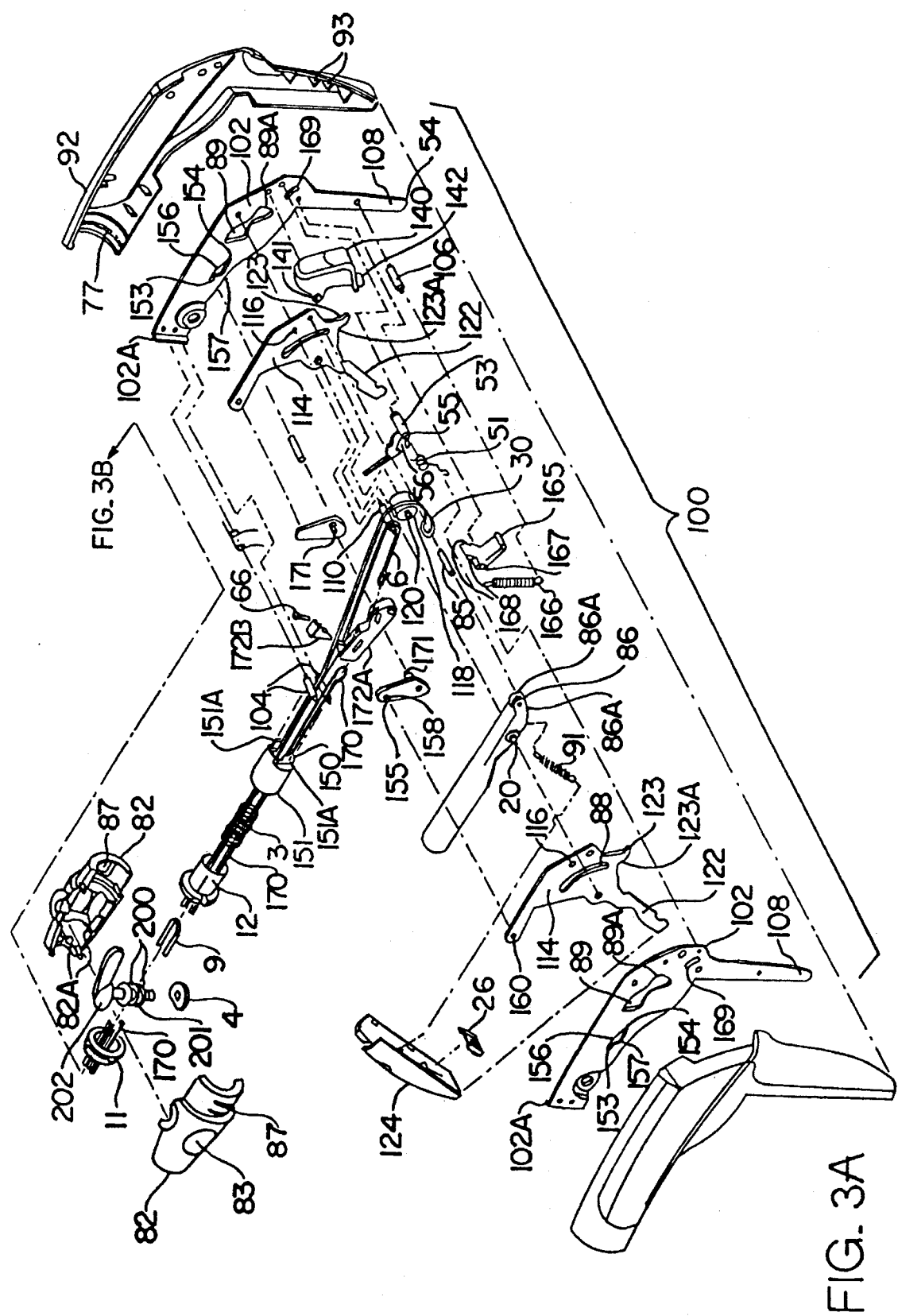

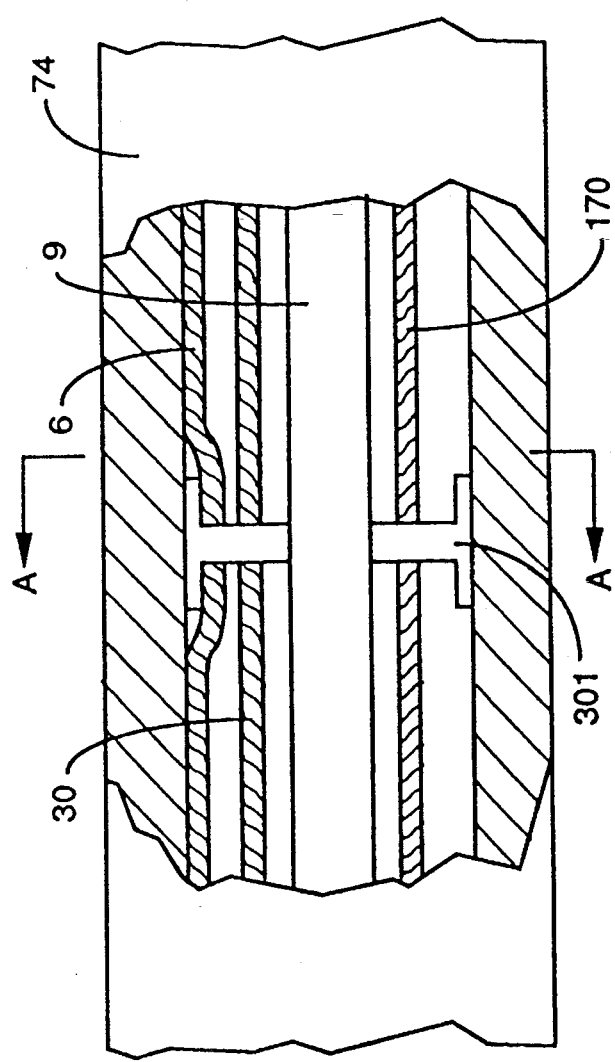
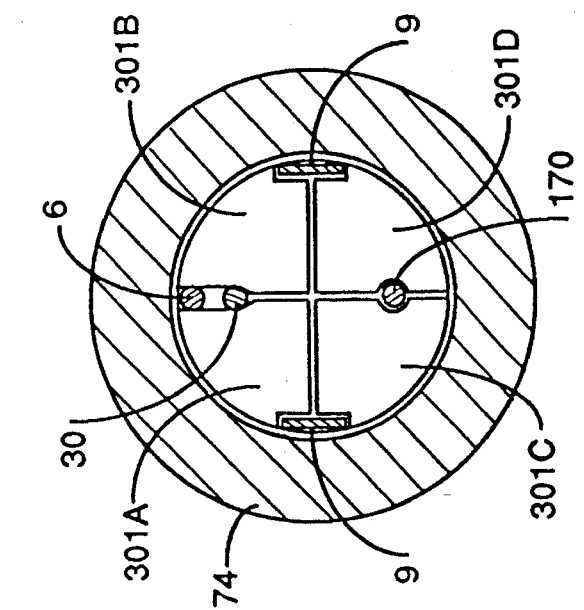
FIG. 11
FIG. 12

HANDLE ACTUATOR FOR SURGICAL INSTRUMENT HAVING CLAMP LOCK AND EMERGENCY RELEASE

This is a division of application Ser. No. 08/219,846 filed Mar. 30, 1994, now abandoned.

FIELD OF THE INVENTION

The present invention generally relates to a surgical instrument for applying surgical fasteners to tissue and, more particularly, to a surgical stapling instrument with an articulated stapling head assembly mounted on a rotatable support shaft to provide more convenient access to restricted surgical sites. Also, this invention relates to a linear surgical stapling instrument including an improved stapling head assembly which is compact in construction, and to an improved actuator handle assembly for closing and firing the stapling head assembly.

BACKGROUND OF THE INVENTION AND PRIOR ART

In recent years, there has been an increasing number of surgeons using surgical staples, rather than conventional sutures, for closing surgical incisions. In part, this is because the use of surgical staples and surgical stapling instruments has made many previously difficult surgical procedures much simpler to perform. Of more importance, however, is that the use of surgical staples significantly reduces the time required for performing most surgical procedures, and therefore reduces the length of time during which the patient must be maintained under anesthetic. Many types of surgical stapling instruments have been devised for different surgical procedures. An added benefit of certain surgical stapling instruments is their ability to be used fluoroscopically or endoscopically, reducing the size of the incision, the amount of patient discomfort, and the amount of recovery time.

The present invention is directed to a surgical instrument for applying surgical fasteners to internal organs and tissues such as the lung, esophagus, stomach, duodenum, and intestines. The invention is embodied in a linear surgical stapler which permits access to restricted surgical sites, e.g., the thoracic region and the pelvic area of the human body.

In its earliest form, the linear surgical stapling instrument was a permanent, multi-use instrument, and the surgical staples were manually loaded into the instrument one at a time.

A subsequent improvement in linear surgical stapling instruments was the development of presterilized, disposable loading units or staple cartridges.

Several types of surgical fastener applying instruments are known for applying surgical fasteners to body tissue clamped between relatively movable fastener holding and anvil portions of the instrument. The surgical fasteners may be metal staples as shown, for example, in U.S. Pat. 3,275,211, or consist of non-metallic resinous materials as shown, for example, in U.S. Pat. 4,402,445. In the case of metal staples, the staple legs are typically driven through the tissue and formed by an anvil to secure the staples in the tissue. In the case of non-metallic fasteners, each fastener may initially consist of two separate parts, i.e., a fastener part disposed in the fastener holding part of the apparatus, and a retainer part disposed in the anvil part of the apparatus. The leg or legs of the fastener parts are driven through the tissue and interlock with the retainer parts to secure the fasteners in the tissue. Although most surgical staples are biologically inert and remain permanently in the body, biologically absorbable metal surgical staples are known. Surgical fasteners of non-metallic resinous materials can also be made either biologically absorbable or non-absorbable.

The surgical instrument of the present invention is not limited to use with any particular type or form of fasteners. The various surgical fasteners mentioned above represent examples of the types of fasteners which can be used with the instrument of the present invention. Thus, as used herein, "surgical fastener" is a term which is generic to all of the above types of fasteners. Similarly, as used herein, "fastener holder" and "anvil" are terms which, except for certain improvements described hereinafter, are generic to surgical instruments for applying all of the above types of fasteners.

In the prior instruments for applying surgical fasteners to tissue clamped between the fastener holding and anvil portions of the instrument, a distal fastener applying assembly is rigidly connected to the proximal actuator portion of the instrument. More recently, however, there has been increasing interest in instruments in which the connection between the fastener applying assembly and the actuator assembly is not completely rigid.

Also, in view of rising hospital costs, there has been an ever-increasing interest in disposable surgical stapling instruments to eliminate as much work as possible, i.e., disassembly, cleaning, reassembly, sterilization and the like, and to be more efficient, while at the same time, not having to compromise the surgical procedures.

SUMMARY OF THE INVENTION

The present invention achieves an improved surgical instrument for applying surgical fasteners, such as staples, to human tissue, which is particularly suited for applying one or more rows of fasteners across a tissue lumen to produce a fluid-tight closure of the lumen. The surgical instrument of this invention is intended for use in thoracic and abdominal surgical procedures in which single fire surgical staplers are currently used and where access to the surgical site is restricted. For example, the surgical instrument can be used in the following types of procedures: (1) a double stapling technique, especially for a low anterior re-section, (2) closure of the bronchus during a lobectomy or pneumonectomy, (3) closure of the esophagus in esophageal procedures, and (4) closure of the pulmonary blood vessels during a lobectomy or pneumonectomy.

The surgical instrument in the present invention comprises a shaft assembly including a support shaft section and a knuckle for articulatably mounting a fastener applying assembly at the distal end of the support shaft with respect to a proximal actuator handle assembly. The fastener applying assembly includes a fastener holder for holding and applying one or more surgical fasteners, a stationary anvil for clamping the tissue using the fastener holder, and a driver for driving the fasteners from the fastener holder into the tissue clamped by the fastener holder against the anvil. The actuator handle assembly includes means for clamping the tissue, actuating the driver, and releasing the tissue after staple forming. The fastener applying assembly is remotely articulated with a joy stick assembly mounted on the support shaft near the proximal end of the instrument. The fastener applying assembly may also be rotated about an axis generally parallel to the longitudinal axis of the support shaft.

In another embodiment of the invention the fastener holder is reloadable, having a removable staple cartridge that may be replaced with a new staple cartridge.

In yet another highly preferred embodiment of the invention, the actuator handle assembly includes a first and second trigger, the first trigger being adapted for closing the fastener holder and anvil relative to each other for tissue clamping and the second trigger being adapted for driving the surgical fasteners into the tissue that has been clamped.

In still another preferred embodiment of the invention, the fastener applying assembly is sized and contoured for insertion between human ribs without the use of rib-spreading devices.

In yet another preferred embodiment of the invention, a flexible cable is used for transferring work from an actuator assembly on the handle of the device to the distal end of the device. This transfer of work, may include, for example, capturing, clamping, and releasing the tissue and driving the surgical fasteners. In a highly preferred embodiment of the invention, the flexible cable comprises a continuous loop of multi-strand braided cable such as Vectran®.

These and other embodiments of the presently preferred invention will become more readily apparent as the following detailed description of the preferred embodiments proceeds, particularly with reference to the figures.

BRIEF DESCRIPTION OF THE DRAWINGS

The foregoing and other objects, aspects and advantages will be better understood and more readily apparent to those of ordinary skill in the art as the following detailed description of the preferred embodiments of the invention proceeds, particularly with reference to the accompanying illustrative figures, in which:

FIG. 11 is a breakaway sectional view of another preferred pressure seal for a preferred embodiment of the invention.

FIG. 12 is a cross sectional view of the embodiment of FIG. 11 taken along lines A—A.

DETAILED DESCRIPTION OF THE PREFERRED EMBODIMENTS

Figure 1:
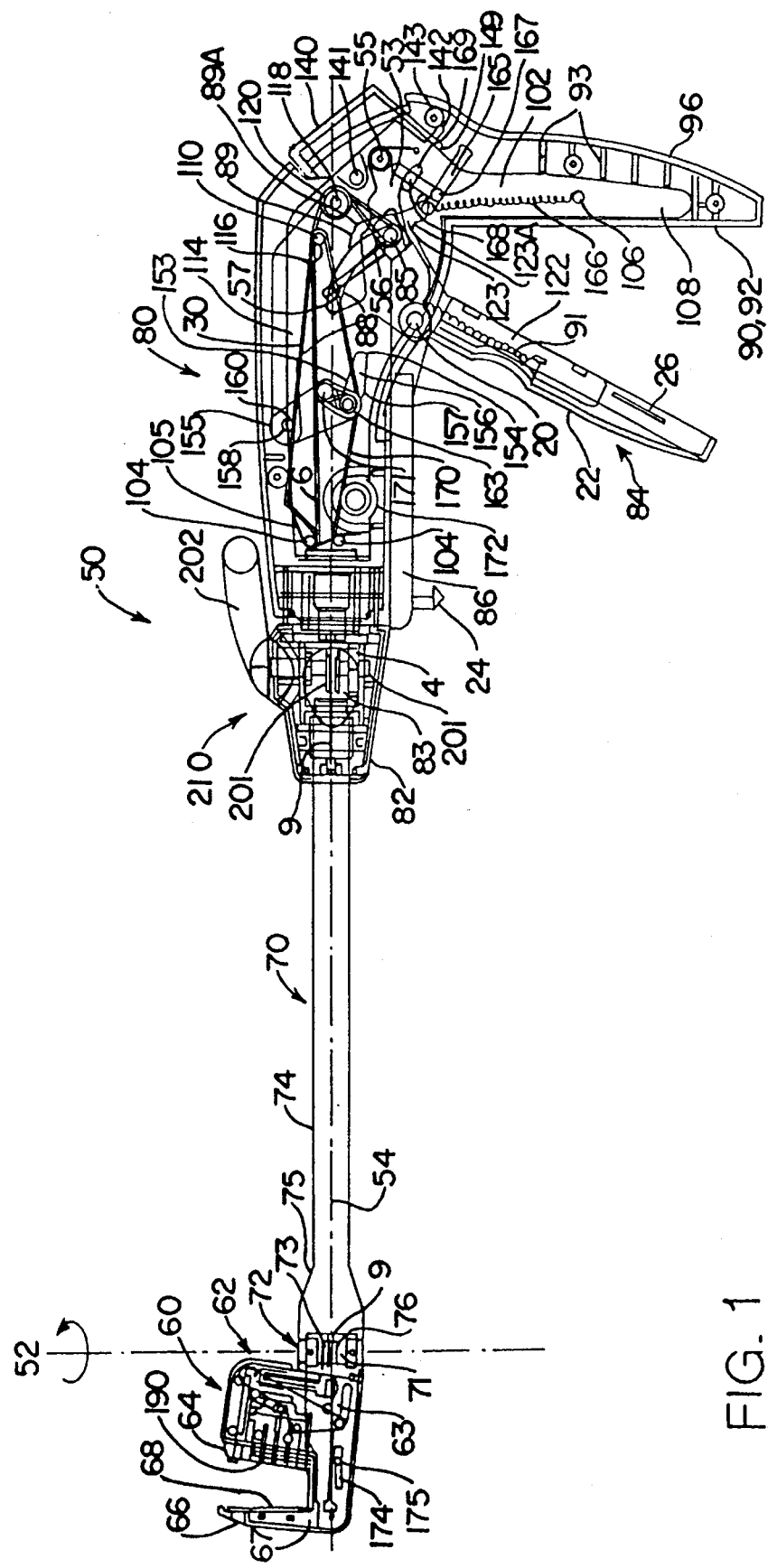
FIG. 1 is a cross sectional, transparent, elevational view of a preferred embodiment of the present invention.
Figure 3B:
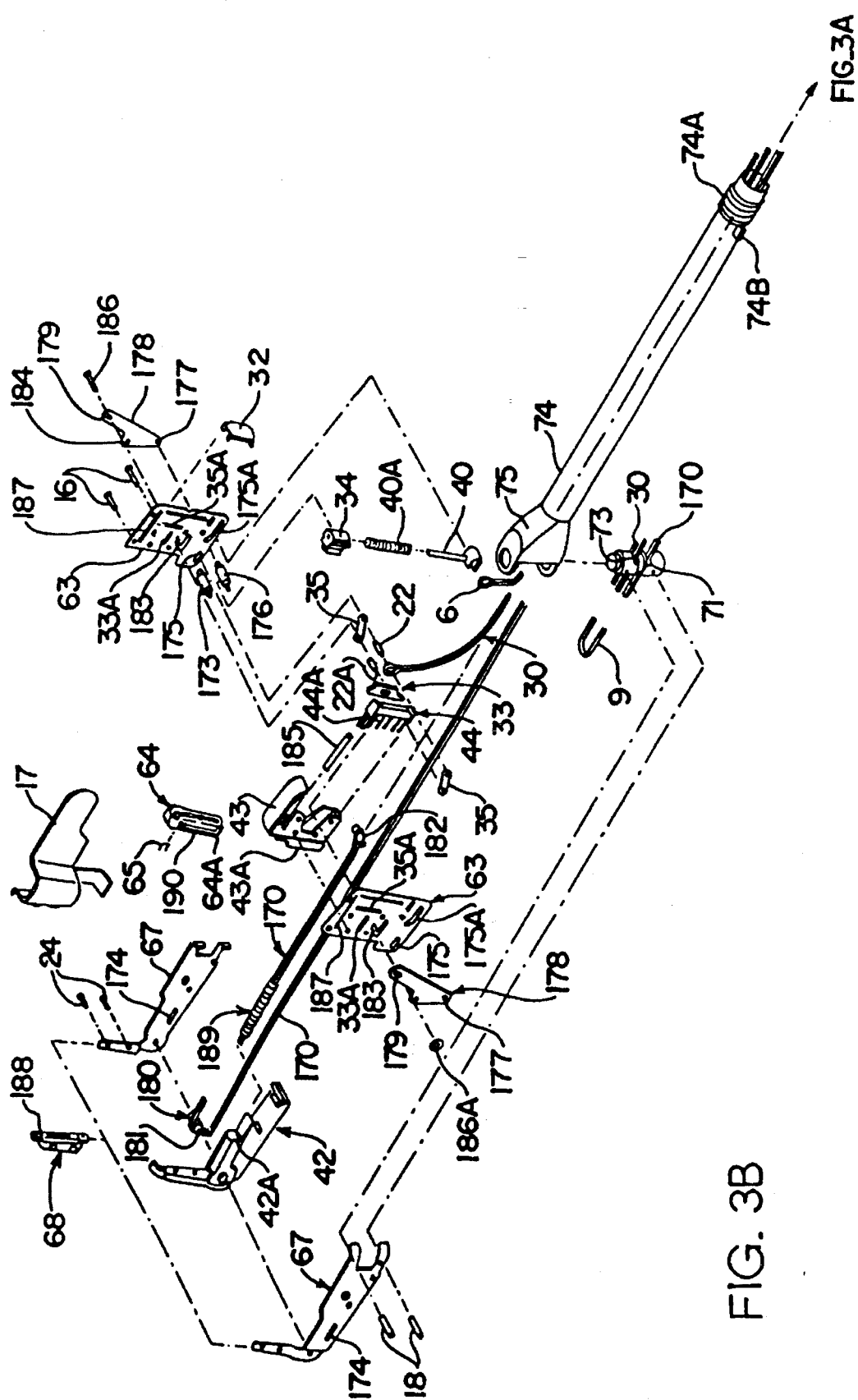
FIGS. 3A and B are exploded isometric views of a preferred embodiment of the present invention.

Referring to FIGS. 1, 3A and 3B, the present invention is embodied in a surgical stapling instrument, generally 50, which includes a distal stapling head assembly, generally 60, connected by a support shaft assembly, generally 70, to a proximal actuator handle assembly, generally 80. The stapling head assembly 60 includes a movable jaw member 62 which supports a staple cartridge 64, and a stationary jaw member 66 which supports a staple-forming anvil 68. The staple cartridge 64 holds one or more rows of staples 65 which are driven against the anvil 68 and formed into a B-shaped configuration to fasten tissue together. For example, fourteen (14) staples may be held in the staple cartridge 64 and arranged in three (3) staggered rows. It will be understood by persons of ordinary skill in the art that the surgical stapling instrument 50 can be adapted to operate with two-part surgical fasteners instead of staples.

The fastener applying assembly 62 is mounted in a hinge-like fashion on a pivot connection or articulation joint, generally 72, which permits the stapling head assembly 60 to pivot or articulate about a vertical axis 52 into different angular orientations relative to a center line or longitudinal axis 54 of the support shaft assembly 70. Preferably, the pivot connection 72 is arranged to allow the stapling head assembly 60 to pivot about the vertical axis 52 in fifteen degree increments. In the preferred embodiment, the stapling head assembly 60 is pivotable either clockwise or counter-clockwise about the vertical axis 52 to positions oriented at ±15°, ±30°, ±45°, ±60°, and ±75° relative to the longitudinal axis or centerline 54. This articulation of the stapling head assembly 60 is achieved remotely with respect to the stapling head assembly 60 via a joystick 202 mounted to the shaft 70 near the handle 80.

The support shaft assembly 70 is rotatably mounted on the actuator handle assembly 80 for rotation about the longitudinal axis or centerline 54. Preferably, the support shaft assembly 70 is rotatable over a range of 180° or more about the centerline 54. A rotation knob 82 is rotatably mounted at the distal end of the actuator handle assembly 80 to allow the support shaft assembly 70 to be placed in a plurality of desired rotational orientations.

The shaft assembly 70 includes a tubular support shaft 74 rotatably mounted on the actuator handle assembly 80 and including a pivot bracket 75 at the distal end of the shaft 74. The pivot bracket 75 may be either integrally formed with the shaft 74, or may comprise a separate component fastened to the shaft 74. The pivot bracket 75 rotatably receives a knuckle pin 76 which is fastened to the stapling head assembly 60. Preferably, the tubular support shaft 74 and the pivot bracket 75 are made of aluminum or a polymeric material, such as Vectra®.

The actuator handle assembly 80 includes a pivotally mounted closure trigger 84 for closing the movable jaw 62 toward the fixed jaw 66 to clamp a section of tissue between the jaws 62 and 66. The actuator handle assembly 80 also includes a pivotally mounted firing trigger 86 for actuating the stapling head assembly 60 to drive the staples from the staple cartridge 64 through the tissue and to form the staples against the anvil 68. The firing trigger 86 is preferably pivotally mounted to the closure lever 84, via a pivot 20. The closure trigger 84 includes a shroud 22 providing the user greater comfort and gripability. The shroud 22 includes an opening for receiving a lock catch 24 on the firing trigger following a staple firing cycle. The shroud 22 further includes a spring-loaded lock/release slide 26, which is slidably received within the shroud. The lock/release slide 26 engages the lock catch 24, locking the firing trigger 86 to the closure trigger 84 as will subsequently be described. The lock/release slide 26 may be slid to release the lock catch 24 and therefore the firing trigger 86 from engagement with the closure trigger at the conclusion of a staple firing cycle.

As shown in FIGS. 1 and 3, the actuator handle assembly 80 includes a pair of hollow handle sections 90 and 92 made of plastic material and adapted to fit together. Each of the handle sections 90 and 92 includes a depending handle grip 96.

Referring to FIGS. 1 and 3–5, the rotation knob 82 has two indented finger grips 83 at diametrically opposed positions to facilitate the manual rotation of the control knob 82 by the surgeon. Preferably, the control knob 82 is mounted for rotation over a range of 180° or more about the longitudinal axis 54 of the support shaft assembly 70. A pair of resilient cams 87 are arranged to engage a set of teeth 77 on the inside of the handle sections 90, 92. The cams 87 and the teeth 77 cooperate in detent fashion to lock the shaft 74 against rotation, but to allow rotation of the shaft 74 in incremental rotational positions upon turning the rotation knob 82 to overcome the forces of locking engagement of the cams 87 with the teeth 77. The cams 87 and the circumferential teeth on the handle sections 90, 92 provide a detent mechanism which defines a plurality of angular positions for rotation of the shaft assembly 70.

The following is a more specific description of particular portions, features, and components comprising highly preferred embodiments of the invention.

Referring to FIGS. 1 and 3A, the actuator handle assembly 80 includes an actuator mechanism, generally 100, contained within the hollow plastic handle sections 90 and 92. Preferably, the components of the actuator mechanism 100 consist of rigid materials, for example, metals, such as stainless steel or aluminum, or a plastic, such as reinforced nylon. The actuator mechanism 100 includes a pair of outer chassis plates 102 which are similar in shape to the handle sections 90 and 92. Each of the handle sections 90 and 92 is provided with a set of internal flanges or ribs 93 which support the chassis plates 102 in a fixed position within the actuator handle assembly 80 when the handle sections 90 and 92 are fitted together. The chassis plates 102 are fastened together in a spaced parallel relationship by a pair of transverse connecting pins or shoulder rivets 104 located adjacent to the distal ends of the chassis plates 102 and by a set pin or shoulder rivet 106 extending transversely between a pair of depending grip portions 108 of the chassis plates 102. An upper connecting pin 110 joins the top middle portions of the chassis plates 102 together. A lower connecting pin (not shown) joins the bottom middle portion of the chassis plates 102 together. Each of the pins 104, 106, 110 support other components of the actuator mechanism 100 as will be described subsequently.

The actuator mechanism 100 includes a pair of closure lever plates 114 each including a pivot hole 116 for receiving the connecting pin 110 to pivotally support the closure lever plates 114 for pivotal movement relative to the chassis plates 102. The closure lever plates 114 are secured together in a spaced parallel relationship by a transverse connecting pin 118 which rotatably supports a pulley 120. The closure lever plates 114 include elongated depending lever portions 122 which are contained inside a hollow plastic closure lever shroud 22 to achieve the closure lever 84 of the actuator handle assembly 80.

The actuator mechanism 100 includes a closure control linkage comprising a toggle link 155 pivotally connected to the distal end of the closure lever plates by a pair of transverse pivot pins 158 (one shown), extending in opposite directions from the upper end of the link 155. The outer ends of each pivot pin 158 extend into a hole 160 in the closure lever plate 114. Another transverse pivot pin or follower pin 163 passes through the lower end of the link 155 and extends into an inclined guide slot 156 formed in each of the chassis plates 102. Each of the guide slots 156 includes an upper distal section 153 and a lower proximal section 154 which overlap and define a detent or shoulder 157 in the guide slot 156.

A closure cable 170, preferably comprising a continuous loop of braided Vectran® cable, manufactured by Hoechst Celanese of Charlotte, N.C., extends from an anchor pin 171 in the toggle link 155 around the transverse pivot pin 163 and around a two-piece pulley sheave 172. The pulley sheave 172 rotates in a lubricated bearing in each of the chassis plates 102, and is expanded or retracted, as needed, acting as a tensioning modulator for the closure cable 170. Optionally, a tension link 172A having a tension pin 172B may be used as illustrated in FIG. 3. The toggle link 155 applies tension to the closure cable 170 when the closure lever plates 114 are actuated by the closure control lever 84. The closure cable 170 extends over the lower coupling pin 104 and through an opening 150 formed in the shaft connector 151.

Figure 2:
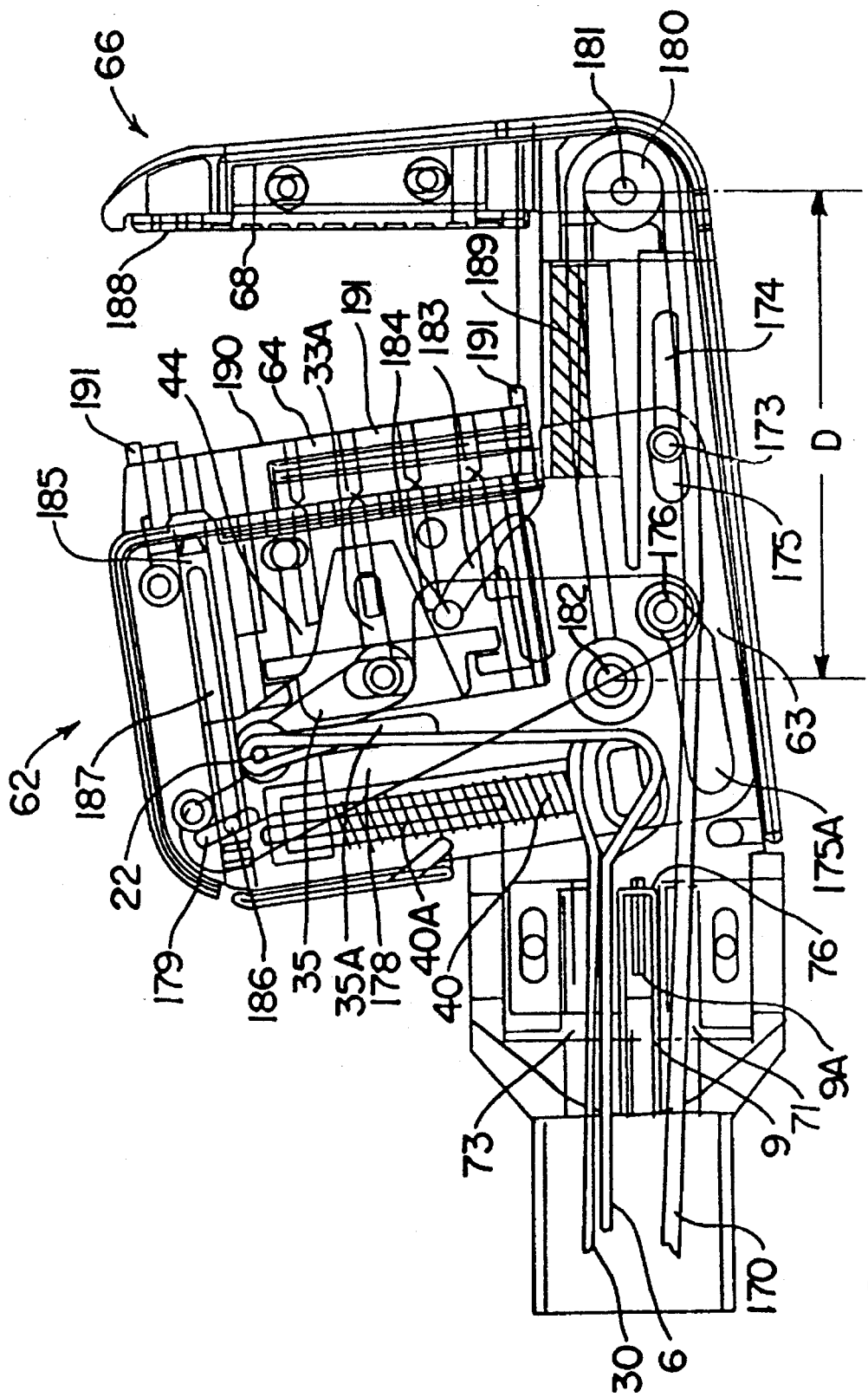
FIG. 2 is a cross sectional, transparent, elevational detail of a preferred staple head assembly of the present invention.

As illustrated in FIG. 3A, the closure cable 170 passes through the approximate center of the distal end of the actuator handle assembly, through the control knob 83, and through the hollow support shaft 74. The cable 170 is preferably coated with a lubricant, such as silicone, to reduce friction. The cable 170 continues through a lower channel 71 in the knuckle pin 76 and into the interior of the staple head assembly 60 as illustrated in FIG. 2. As illustrated in FIGS. 2 and 3B, the closure cable 170 continues through a hole or channel 42A in the body of the staple head pilot 42 to the distal end of the staple head assembly 60 and passes around a head pulley 180 rotatively mounted via a head pulley axle 181 passing through to the anvil side plates 67 which support the anvil 68 on either side thereof. The closure cable 170 reverses direction at the head pulley 180, making a 180° bend, and continues through the staple head assembly 60, passing through an opening spring 189, which biases the movable jaw 62 apart from the anvil 68. The closure cable 170 terminates at an anchor pin or closure rivet 182.

As the closure trigger 84 is pulled proximally toward the handle 96, the closure cable 170 is also pulled rearwardly, which causes the distance D between the axis of the head pulley 180 and the anchor pin 182 to shorten, pulling the movable jaw 62 toward the fixed jaw 66.

The movable jaw 62 includes a double shoulder roller pin 173 that is captured by a horizontal slot 174 in each of the anvil side plates 67. This slot 174 is actually disposed at a slight incline with respect to the axis 54 of the shaft 74. The double shoulder roller pin 173 is also retained within a forward slot 175 in each of the head plates 63 on either side of the movable jaw 62. As the movable jaw 62 proceeds distally, toward the anvil 68, the double shoulder roller pin 173, in conjunction with the slots 174 and 175, and the stationary pin 176 in conjunction with the slots 175A assist in orienting the clamping surface 190 of the staple cartridge 64 generally parallel to an opposing surface comprising the anvil 68.

Referring to FIGS. 2 and 3B, each of the head plates 63 of the movable jaw 62 further includes a dogleg slot 175A which receives a stationary pin 176 passing through a hole 177 in a pair of pin placement arms 178. Each pin placement arm 178 includes an upper slot 179. A placement pin 185, slidably positioned in the movable jaw 62, includes a horizontal alignment pin 186 that passes through the placement pin 185 and through both the upper slot 179 in the pin placement arm 178 and a horizontal upper slot 187 in the head plate 63. The alignment pin 186 is retained with a groove washer 186A. As the movable jaw 62 proceeds distally toward the anvil 68, the pin placement arm 178 is forced to rotate about the stationary pin 176 in a clockwise direction, which forces the placement pin 185 to move distally toward the anvil 68.

By the time the transverse pivot pin 163 of the toggle link 155 has come to rest behind the inclined shoulder portion 157 of the inclined guide slot 156, by virtue of the closure trigger 84 being pulled rearwardly, the placement pin 185 has emerged from the movable jaw 62 and becomes seated within a hole 188 in the upper end of the anvil 68. At this point, any tissue positioned between the clamping surface 190 and the anvil 68 is captured by the placement pin 185, in combination with the clamping surface 190 and anvil 68.

The stationary pin 176 acts as a pivot about which the pin placement arm 178 may rotate. This rotation is achieved by virtue of a V-shaped slot 183 in the head plate 63. A short pin 184 near the leading edge of the pin placement arm 178 rides within the V-shaped slot 183. As the movable jaw 62 moves toward the anvil 68, this short pin 184 is forced along an arcuate path roughly corresponding to that of the curved portion of the V-shaped slot 183. This in turn causes the upper section of the pin placement arm 178 to rotate, which, through the upper slot 179, causes the alignment pin 186 to slide along the placement pin slot 187, forcing the placement pin 185 toward the anvil 68.

As the closure trigger 84 continues to be pulled toward the handle 96, the clamping surface 190 of the movable jaw 62 clamps down against the tissue captured between the clamping surface 190 and the stationary anvil 68. At the same time, a trigger lock 165 in the handle assembly 80, which is biased forwardly by a spring 166, begins to pivot in a clockwise direction (FIG. 1) about a pivot pin 167 that passes through the chassis plates 102. A guide pin 168 in an upper leg of the trigger lock 165 rides in an arcuate slot 169 in the chassis plates 102. The rear of the elongated lever portion 122 of the closure trigger 84 includes a flange 123, which forces the trigger lock 165 to pivot about the trigger lock pivot pin 167 as the closure trigger 84 is pulled toward the handle 96. Upon complete closure of the closure trigger 84, the flange 123 rides over the guide pin 168. The guide pin 168 in turn is pulled forward by the biasing spring 166, coming to rest at the forward end of the arcuate slot 169, where it retains the flange 123 by seating in the notched portion 123A thereof. Once this position has been achieved, the clamping cycle is complete, and the closure lever 84 is locked into place, in a substantially vertical position, parallel to the handle 96.

The trigger lock 165 is engaged by a release button 140, which can be depressed to release the trigger lock 165, as will now be described. The release button 140 includes a pivot pin 141 passing through a hole in the chassis plates 102. The release button 140 further includes a rearward flange 142, which is captured by a pin or rib 143 in the handle sections 90, 92. The release button 140 further includes a forward flange 149 that abuts the trigger lock 165 when the release button 140 is depressed.

In order to utilize the release button 140, it is first necessary to overcompress the closure trigger 84 toward the handle 96, thereby releasing the pressure of the closure trigger flange 123 on the trigger lock guide pin 168. Once this has been accomplished, the release button 140 may be depressed, forcing the guide pin 168 toward the rear of the arcuate slot 169, clearing the flange 123. This, in turn, allows the moveable jaw 62 to return to an open position by virtue of the opening spring 189, returning the closure trigger 84 to an open position.

A highly desirable feature of the present invention is that the staples may not be fired until the closure trigger 84 has been fully engaged, thereby clamping the tissue to be stapled. Once this has been accomplished, as previously described, the firing sequence is ready to take place.

As the closure trigger 84 is pulled toward the handle 96, the firing trigger 86 begins to descend from its initially horizontal position, ultimately achieving an orientation of roughly forty five degrees (45°) with respect to the longitudinal axis 54 of the shaft 70. The closure trigger 84 and firing trigger 86 work in cooperation with one another by virtue of a trigger pin 85 that passes through both the closure lever 122 of the closure trigger 84 and the proximal end of the firing trigger 86. This trigger pin 85 rides within an arcuate slot 88 contained in the closure lever 122. As the closure trigger 84 is drawn rearwardly, the trigger pin 85 is forced to ride up along the rear of a bow tie-shaped opening 89 in the chassis plates 102. The closure lever plate 114 and therefore the closure lever 122 rotate about the connecting pin 110, which also serves as a pivot. After the closure trigger 84 has been fully closed, the trigger pin 85 comes to rest at a position 89A corresponding to the upper rear corner of the bow tie-shaped slot 89. At this point, the arcuate slot 88 has rotated forward, such that the trigger pin 85 is free to advance as the firing trigger 86 is pulled.

The firing trigger 86 is biased apart from the closure trigger 84 by a biasing spring 91.

A firing cable 30, which may be the same type of cable used for the closure cable 170 previously described, is anchored to the firing pin 85 by looping the firing cable 30 around the firing pin 85 as illustrated in FIGS. 1 and 3A. This loop of the firing cable 30 is retained in the firing pin 85 by a pair of flanges 86A on the firing trigger 86. The two strands of firing cable 30 wrap around a pulley 120 and pass over a tensioning spring 105 anchored by the transverse connecting pins 104. The firing cable 30 continues through the device by passing through the shaft 74 and through a channel 73 through the knuckle pin 76 as illustrated in FIGS. 2 and 3B.

As best seen in FIGS. 2 and 3B, the firing cable 30 enters the movable jaw 62 horizontally, looping around the underside of a driver return pin 40 that passes through a driver return spring 40A. The firing cable 30 changes direction at the base of the driver return pin 40 and proceeds vertically to a firing link pin 22. The firing link pin 22 passes through the upper end of a dog-bone shaped firing link 35 and through a vertical slot 35A and the head plates 63. A second firing link pin 22A passes through the lower portion of the firing link 35, through a strong back plate 33, and through a horizontal slot 33A in the head plates 63. The strong back plate 33 is received by a staple driver 44, which drives staples 65 from the staple cartridge 64.

The staple driver 44 is slidably received within a staple head casing 43 as illustrated in FIG. 3B. The staple head casing 43 includes a pair of flanges 43A for slidably receiving the removable/reloadable staple cartridge 64. This is accomplished by a pair of complementary flanges 64A in the staple cartridge 64, which slide within grooves in the flanges 43A of the staple head casing 43.

As seen in FIG. 2, the clamping surface 190 of the staple cartridge 64 includes one or more projections 91 which abut the innermost surface of the anvil 68, creating a predetermined space between the clamping surface 90 and the anvil 68. This space is roughly equivalent to the height of the projections 191. The height of the projections 191 determines the size of the staple formed by the stapling procedure, as will be subsequently described.

As shown in FIG. 3B, a pilot 42 having a tapered frontal portion comprises the leading edge of the staple head assembly 60. This pilot 42 is sized and shaped to a narrow, tapered contour, to provide access of the staple head assembly 60 between adjacent ribs of a patient without the need for rib-spreading techniques or instruments as was necessary in the prior art. This narrow contour of the pilot 42 is made possible by virtue of the unique combination of elements of the present invention, including by way of example, the stationary anvil 68, the tight-radiused pulley 180 allowing for the reverse direction of the closure cable 170, and the use of a sufficiently flexible closure cable 170 that does not take a set following the 180° bend about the pulley 180.

The staple firing operation of the present invention proceeds as follows. After the closure trigger 84 has been fully closed as previously described, the operator grasps the firing trigger 86 and pulls same toward the handle 96. This causes the firing cable 30 to be pulled rearwardly about the pulley 120, which causes the vertical portion of the firing cable 30 to pull the firing link pin 22 vertically downwardly in the slot 35A. This, in turn, pushes the lower portion of the firing link 35 and lower firing link pin 22A horizontally through the horizontal slot 33A, which drives the strong back plate 33 toward the anvil 68. The strong back plate 33 in turn drives the staple driver 44 into the staple cartridge 64, which causes staples 65 to be driven into the anvil 68, where they are formed in and about tissue clamped between the anvil and the clamping surface 190.

The degree of lateral movement of the staple driver 44 is limited by the base of the driver 44, which supports staple driver arms 44A, which base contacts a rearward surface of the staple casing 43 upon completion of a firing cycle. Alternatively, the lateral movement of the staple driver 44 may be limited by the length of the link 35 or the length of the horizontal slot 33A. As previously described, the forward or lateral movement of the staple cartridge 64 is limited by the projections 191. Thus, by varying the height of the projections 191 from one staple cartridge to the next, the relative size of staples being used and/or formed may be varied as well.

As previously discussed, when the staple firing trigger 86 is fully closed, a lock catch 24 on the firing trigger 86 engages a lock/release slide 26 on the closure trigger 84. Once this locking is achieved, the release button 140 must be deployed to release the triggers 84 and 86 from a vertical position. At this point, the lock/release slide 26 may be deployed to release the firing trigger 86 from the closure trigger 84.

When the firing trigger 86 is released, the firing cable 30 moves distally, or forwardly, within the staple head assembly 60, releasing the compressive forces placed on the driver return pin 40 and driver return spring 40A, causing the driver return spring 40A to extend upwardly, forcing the driver return lever 34 upwardly, causing the firing link 35 to pull the strong back plate 33 and staple driver 34 rearwardly, away from the anvil 68.

Referring to FIGS. 1 and 3A, a highly preferred embodiment of the invention includes a safety lock 53. The safety lock 53 includes a pivot 55 that passes through a hole in the chassis plates 102. The safety lock 53 includes a recess 56 that receives the trigger pin 85 passing through the firing trigger 86. The recess 56 precludes actuation of the firing trigger 86 until the closure trigger 84 is pulled vertically and snaps into place proximate the handle 96. Once this has occurred, the safety lock 53 rotates about the pivot 55 upwardly such that the recess 56 becomes substantially aligned with the arcuate slot 88, clearing a pathway for the trigger pin 85 to pass, thereby allowing actuation of the firing trigger 86.

The safety lock 53 is biased by a safety lock spring 51. Upon completion of the firing cycle and return of the closure trigger 84 and firing trigger 86 to their open position, the biasing spring 51 pivots the safety lock 53 back to the position illustrated in FIG. 1. An inclined shoulder 57 allows the trigger pin 85 to slide past the safety lock 53 and return to seat within the safety lock recess 56 as illustrated in FIG. 1.

In a highly preferred embodiment of the present invention, a release cable 6 is provided, which is anchored to the anchor pin 171 of the toggle link 155, loops around the connecting pin 110, passes between the transverse connecting pins 104, through the shaft connector 151, through the shaft 74 and loops around the base of the driver return pin 40.

When the physician encounters a jammed staple and/or clamping scenario, the jam may be released by simply deploying the closure trigger 84 away from the handle 96, using the release button 140 if necessary to enable deployment of the trigger. This procedure pulls the release cable 6 rearwardly about the connecting pin 110, which pulls the driver return pin 40 rearwardly, separating the staple cartridge 64 from the anvil 68 substantially as previously described.

In a most highly preferred embodiment of the invention, the staple cartridge 64 is removable and replaceable, allowing the surgical instrument 50 to be reloaded with staples contained in a new staple cartridge 64 following a stapling procedure. As illustrated in FIG. 3B, the staple cartridge 64 includes one or more flanges 64A that are slidably received within a groove contained in complementary flanges 43A in the staple head casing 43. These flanges may further include a locking flange for snapping the staple cartridge 64 in place. Because the staple cartridge 64 is removable, it may be replaced by a second staple cartridge 64 having differently sized staples, enabling the same instrument 50 to apply more than one size of surgical staple. As previously described, the staples 65 may themselves have a different size or shape or the projections 191 on the clamping surface 190 of the staple cartridge 64 may be varied from one staple cartridge to another, varying the height of a staple formed by the stapling instrument.

Preferably, the staple cartridge comprises a unitary piece such as plastic, having one or more channels for slidably receiving the staple driver as previously described. Because the staple driver 44 is slidably positioned within the staple head assembly 60, and is retracted from the staple cartridge 64 following a staple firing cycle as previously described, the staple driver 44 remains within the staple head assembly 60 following removal of the staple cartridge 64.

The cables 6, 30, and 170 of the invention may be fabricated of any sufficiently flexible cable that does not take a set when reversing direction, for example, by being wrapped around the tightly radiused pulleys and pins of the present invention. A highly preferred embodiment of the invention utilizes Vectran® cables comprised of multi-strand braided Vectran® fibers. Because this material is quite slippery, it has proven helpful to use a continuous loop for each of the cables as previously described, both ends of the loop being wrapped around appropriate pins or pulleys as discussed herein.

An additional safety feature of the present invention involves the placement pin 185, which, in addition to providing alignment of the cartridge 64 and anvil 68 also acts as a safety lock, locking the staple cartridge 64 within the staple head assembly 60 during the clamping and staple firing cycles, preventing the staple cartridge 64 from being removed from the staple head assembly 60 until the closure trigger 84 is released from its locked position following the clamping operation.

A highly preferred embodiment of the invention incorporates a mechanism for articulating, and preferably remotely articulating the staple head assembly 60 about the vertical axis 52 of the knuckle pin 76.

As illustrated in FIGS. 1 and 3A, a highly preferred mechanism for articulating the staple head assembly 60 includes an articulation assembly, generally 210, including a joystick or articulation lever 202 having a vertical shaft 201 that extends into the body of the instrument 50, passing through the control knob 82. The joystick shaft 201 includes a pair of annular flanges 200. A continuous articulation belt, 9, rides between the flanges 200 of the joystick vertical shaft 201 and passes through the hollow shaft 74 to the knuckle pin 76. As illustrated in FIG. 2, the belt 9 is secured to the knuckle pin 76, for example, with a pin 9A passing through the belt 9 and being fastened within the knuckle pin 76. This pin 9A assists in preventing the belt 9 from slipping during the articulation operation.

Figure 4:
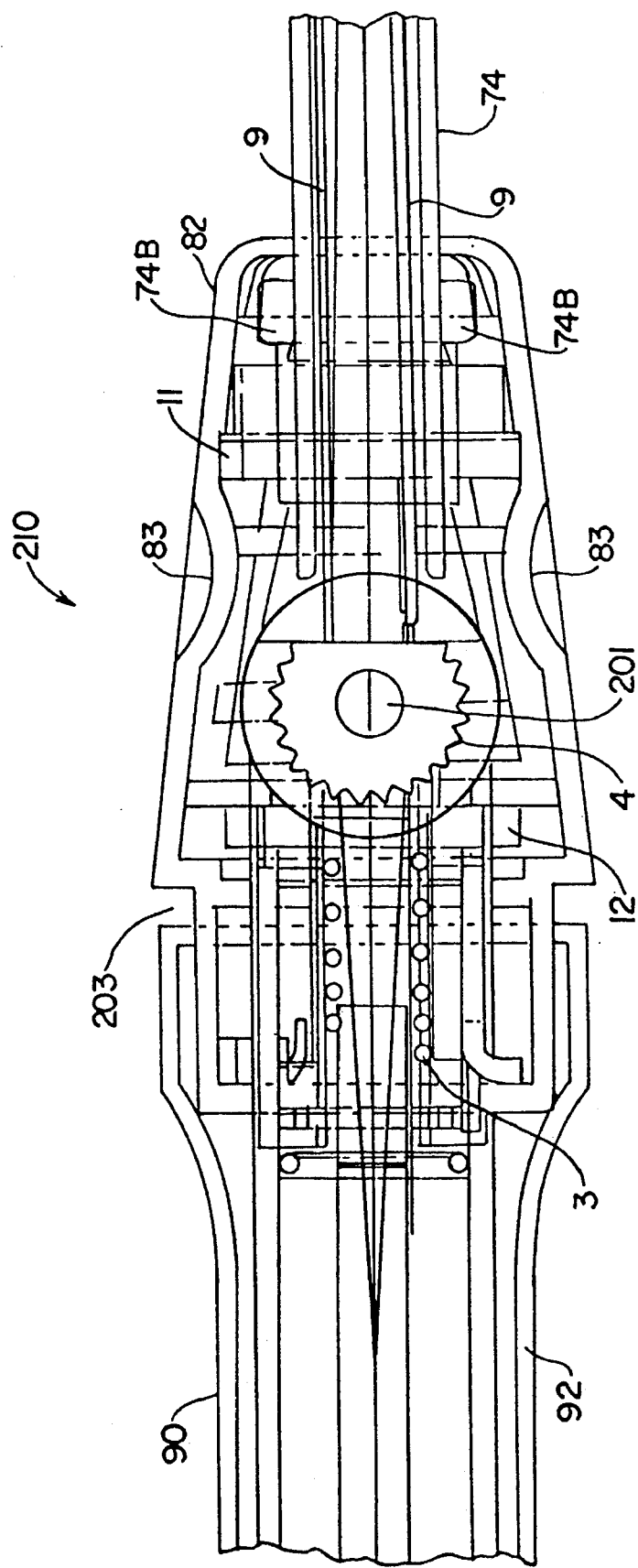
FIG. 4 is a transparent top plan sectional view of a preferred articulation assembly of the present invention.
Figure 5:
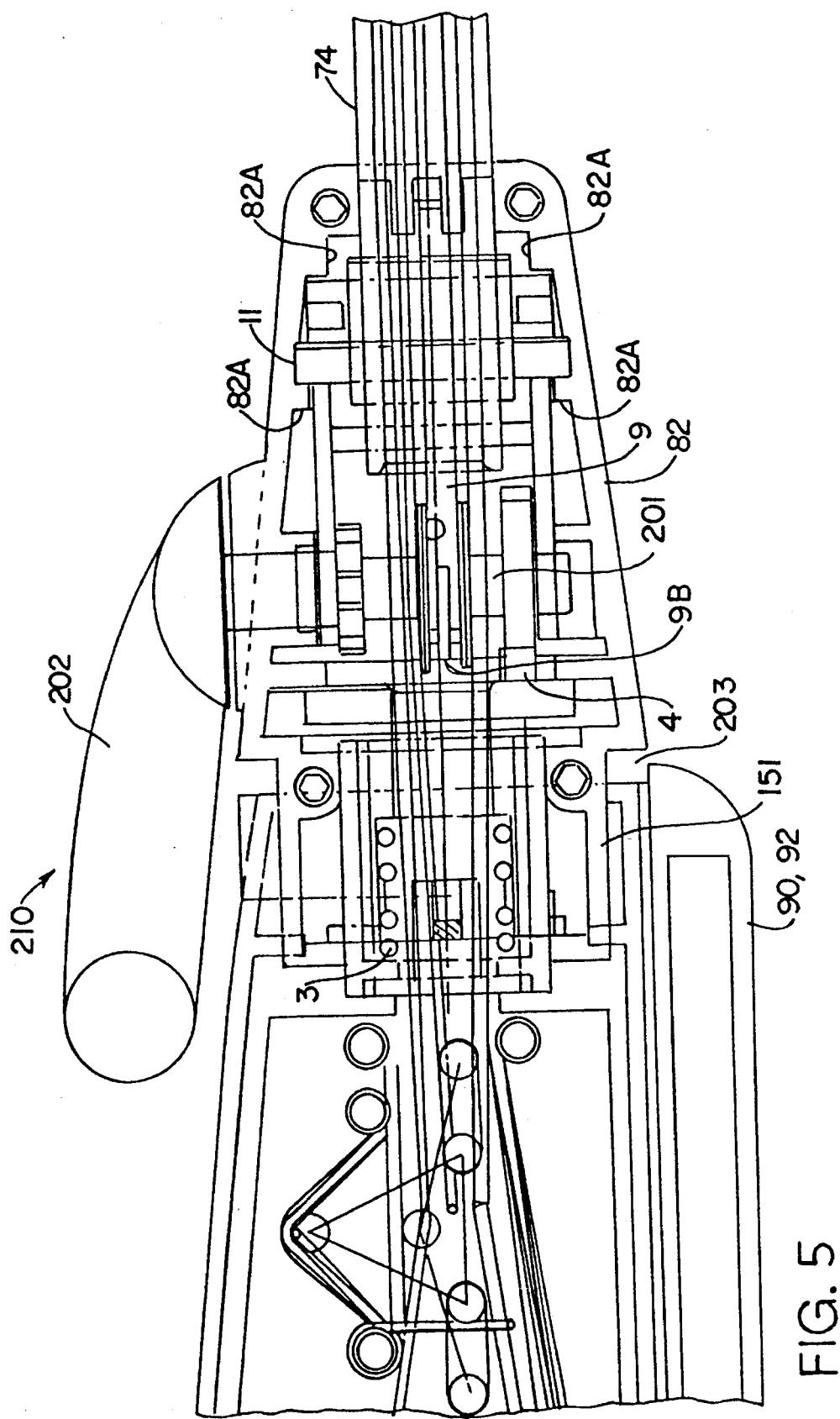
FIG. 5 is a cross sectional, transparent, side elevation of the articulation assembly of FIG. 4.

Referring now to FIGS. 4 and 5, the details of a preferred articulation mechanism of the present invention are illustrated. The shaft 201 of the joystick 202 receives a clutch gear 4, having a series of teeth which engage a complementary set of notches in a cylindrical bushing 12 which is biased distally against the clutch gear 4 by an articulation spring 3.

A nut 11 is threadably received by threads 74A (FIG. 3B) on the proximal end of the tubular support shaft 74. This nut 11 is captured by flanges 82A on the inside of the control knob 82, providing location for the nut 11. Flanges 74B on the shaft 74 prevent relative rotation of the control knob 82 and the shaft 74. Rotation of the nut 11 causes translation of the shaft 74 relative to the control knob 82, providing for tolerance compensation of the assembly. The joystick shaft 201 is rotatably received within the control knob 82 as previously discussed. The articulation belt 9 loops around the articulation lever shaft 201 and is secured thereto with a pin 9B to prevent slippage in the same way that the pin 9A prevents slippage of the belt 9 around the knuckle pin 76.

The articulation assembly 210 is connected to the handle assembly 80 by a cylindrical shaft connector 151 that has a pair of flanges 151A that are captured by a pair of capture flanges 102A in the chassis plates 102.

When the articulation lever or joystick 202 is rotated, it causes the shaft 201 to rotate, which transfers work via the articulation belt 9 to the knuckle pin 76, causing the staple head assembly 60 to rotate about the axis 52. In the embodiment of FIGS. 1–5, this articulation occurs in 15 degree increments dictated by the teeth of the clutch gear 4 and bushing 12.

The articulation spring 3 releasably retains the clutch gear 4 and hence the staple head assembly 60 in a particular angle of articulation. When it is desired to alter this angle, the operator need only overcome the compressive forces exerted by the articulation spring 3 on the clutch gear 4 by rotating the articulation lever 202. This causes the clutch gear 4 to displace the bushing 12 rearwardly, until the teeth in the clutch gear 4 disengage from the notches in the bushing 12, recede, and rotate to a new set of notches, at which point the bushing 12 slides distally toward the clutch gear 4, locking the clutch gear 4 and staple head assembly 60 in its new articulation position. As the closure trigger 84 continues toward the handle 96, tension in the closure cable 170 compresses the articulation spring 3, causing the articulation assembly 210 to translate proximally, closing the gap 203 between the control knob 82 and the handle sections 90, 92. When this translation occurs, the shaft connector 151 contacts the bushing 12, preventing the bushing 12 from displacing rearwardly, thus preventing the teeth in the clutch gear 4 from disengaging from the notches in the bushing 12. This action effectively locks the articulation lever or joystick 202, which prevents movement of the articulation belt 9 and the knuckle pin 76 and therefore prevents rotation of the staple head assembly 60 about the axis 52. When the closure trigger 84 is released, the articulation spring 3 returns the mechanism to its original configuration. This locking mechanism, when employed, preferably precludes use of the instrument (i.e., clamping and/or stapling) at articulation positions other than the increments dictated by the teeth of the clutch gear 4 and bushing 12.

Another highly preferred embodiment of the invention is illustrated in FIGS. 6–9. In this embodiment, an improved device, generally 700, for pivoting, or articulating the staple cartridge 100 with respect to the support shaft assembly 70 is illustrated. The device includes a control knob 702 rotatably mounted on the support shaft assembly 70 proximate the actuator handle assembly 80. The control knob 702 is preferably mounted to the support shaft assembly 70 and rotates about an axis A4 generally perpendicular to the longitudinal axis A1 of the support shaft assembly 70.

Figure 6:
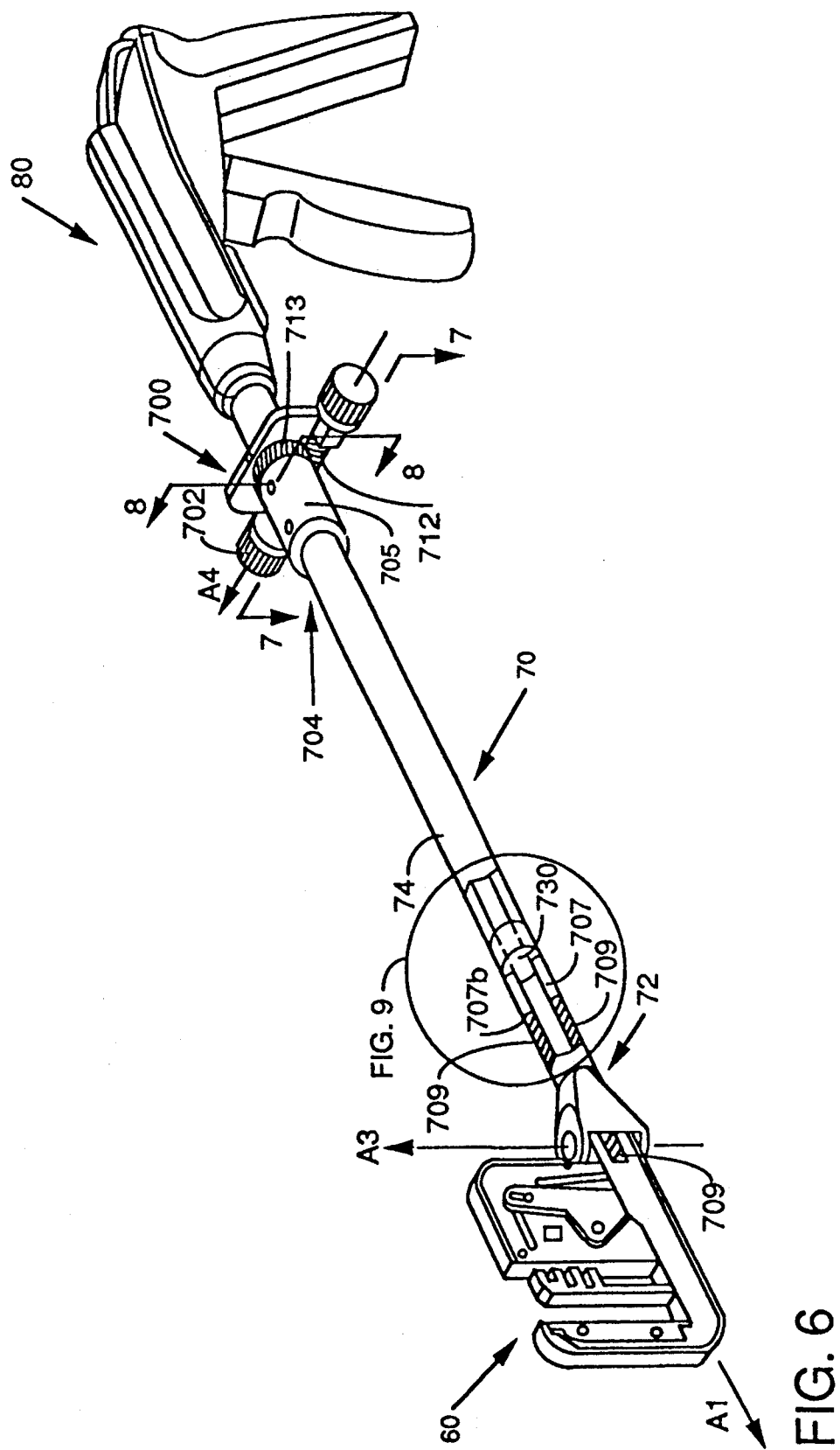
FIG. 6 is an isometric view of another preferred embodiment of the invention having a sweeping articulation assembly.
Figure 7:
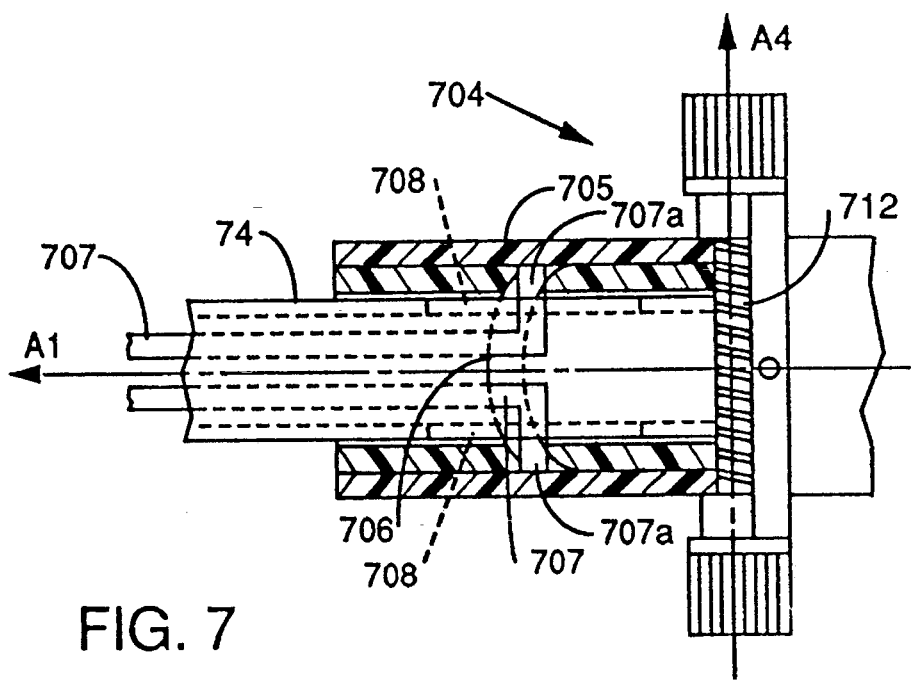
FIG. 7 is a top plan partial cross sectional view of the articulation assembly of FIG. 6, taken along lines 7—7.

The control knob 702 is adapted for transferring rotational motion of the control knob to an articulation driver assembly, generally 704, in a longitudinal direction generally parallel to the longitudinal axis A1 of the support shaft assembly 70. Preferably, the articulation driver assembly comprises a sleeve 705 rotatably positioned on the support shaft assembly 70. The sleeve 705 has an annular channel 706 therein. As illustrated in FIGS. 6–9, the tubular support shaft 74 slidably receives a pair of rods 707. Each of the rods 707 has a flange 707A extending perpendicularly from the proximal end of the rod 707. Each flange 707A in turn passes through and rides along a pair of slots 708 on either side of the tubular support shaft 74, the slots 708 preferably being oriented generally parallel to and coplanar with the axis A1 of the shaft 74. The flanges 707A also ride within the annular channel 706 of the sleeve 705. As illustrated in FIGS. 6 and 9, each of the rods 707 may slidably ride within a guide 730 inside the tubular support shaft 74 for maintaining spacing between the rods 707 and the walls of the tubular support shaft 74.

Referring again to FIGS. 6–8, the control knob 702 preferably includes a worm gear 712 about the control knob axis A4 for transferring rotational motion about the control knob axis A4 to rotational motion about the support shaft longitudinal axis A1. This is preferably accomplished with an annular gear 713 fastened to the sleeve 705.

Figure 8:
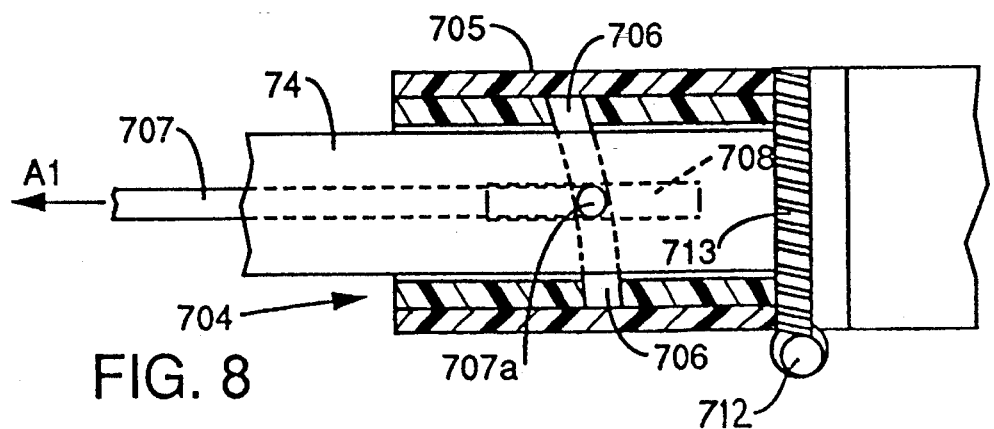
FIG. 8 is a side elevational partial cross sectional view of the articulation assembly of FIG. 6, taken along lines 8—8.
Figure 9:
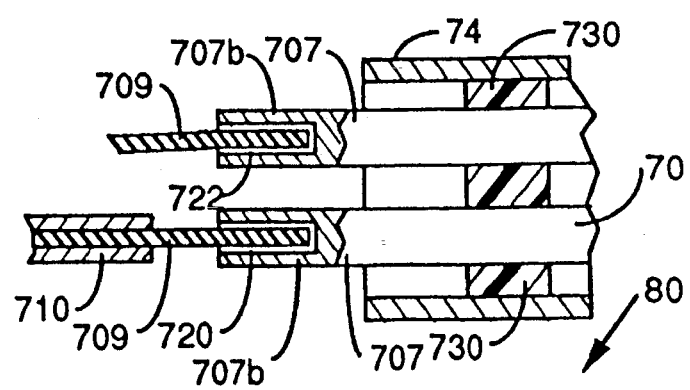
FIG. 9 is a cross sectional detail of the encircled portion of FIG. 6.

As further illustrated in FIG. 8, the annular channel 706 of the sleeve 705 has an inclined orientation with respect to the longitudinal axis A1 of the support shaft assembly 70. This inclined orientation converts the rotational motion of the sleeve 705 and annular channel 706 to the longitudinal motion of the flange 707A within the slot 708 when the sleeve 705 is rotated.

As best seen in FIG. 9, each rod 707 has connected to its distal end 707b a flexible cable 709 which may be pushed and pulled by the rod 707 as its flange 707A slides in the slot 708 and as the rod 707 slides in the tubular support shaft 74. Preferably, each rod end 707B has a blind hole 720, which receives the cable 709 as illustrated in FIG. 9. As illustrated, the cable 709 is slipped into the blind hole 720 and secured to the rod 707, for example, with a crimp or an adhesive material 722. Each flexible cable 709 is connected at its distal end to the staple head assembly 60 as illustrated. In making this connection, the cable 709 is fed through the hollow tubular support shaft 74, through the pivot connection 72 and attached to the staple head assembly 60 at a point in the plane parallel to that formed by the intersection of the axes and A1 and A3, but at a point spaced from the axis A3. Preferably, this connection between the cable 709 and the staple head assembly 60 is achieved by passing the cable 709 into a hole or bore in the staple head assembly 60, with an adhesive or any other acceptable fastening method.

The flexible cables 709 may be fabricated of any materials suited for the purpose including, by way of example, but not limitation, steel, nitinol, nylon, and fiberglass. The flexible cable 709 preferably retains good flexing memory.

In a highly preferred embodiment of the invention illustrated in FIG. 9, the flexible cables 709 are slidably received within a flexible sleeve 710, which provides reduced friction as the cable 709 is pushed and/or pulled through the tubular support shaft 74. The flexible sleeves 710 are preferably fabricated of fiberglass reinforced or steel reinforced nylon, Teflon®, polyethylene, among other equivalent materials known in the art.

The embodiment illustrated in FIGS. 6-9 is a "push/pull" system. That is, when one of the cables 709 is in compression, the other cable 709 is in tension as dictated by the rotation of the sleeve 705. As illustrated in FIG. 6, the length of the cable 709 is relatively short with respect to the length of the tubular support shaft 74 and rods 707, enabling each cable 709 to be pushed without buckling substantially. Buckling is further avoided by the use of the flexible sleeves 710.

In addition to a "push/pull" system, it would also be possible to arrange the embodiment of FIGS. 6-9 in either a "pull/pull" or a "push/push" system, whereby both cables are pulled or pushed, respectively. For example, in a "pull/pull" system, Vectran® cables, similar to those previously described, could be looped around the flanges 707A, which could be replaced with a pin passing through both slots 708. The distal end of the cables could be looped around anchor pins in the staple head assembly 60, on either side thereof. Thus, pulling one Vectran® cable would articulate the staple head assembly 60 in the direction of pull. Pulling the other cable would reverse the direction of articulation.

The articulation assembly 700 of the invention offers several advantages with respect to prior articulation devices. The assembly 700 allows a complete sweep of articulation over the entire range of articulation (generally 0°–75°), rather than the more limited fixed angles of articulation provided with a detent mechanism. Additionally, because of the use of the worm gear mechanism, with its advantageous gear ratios, preferably greater than 2:1 to prevent backdriving (i.e., a situation wherein external forces on the staple head cause the head to tend toward an undesirable orientation), the degree of articulation is both precisely and easily controlled with the turn of the control knob 702.

Figure 10:
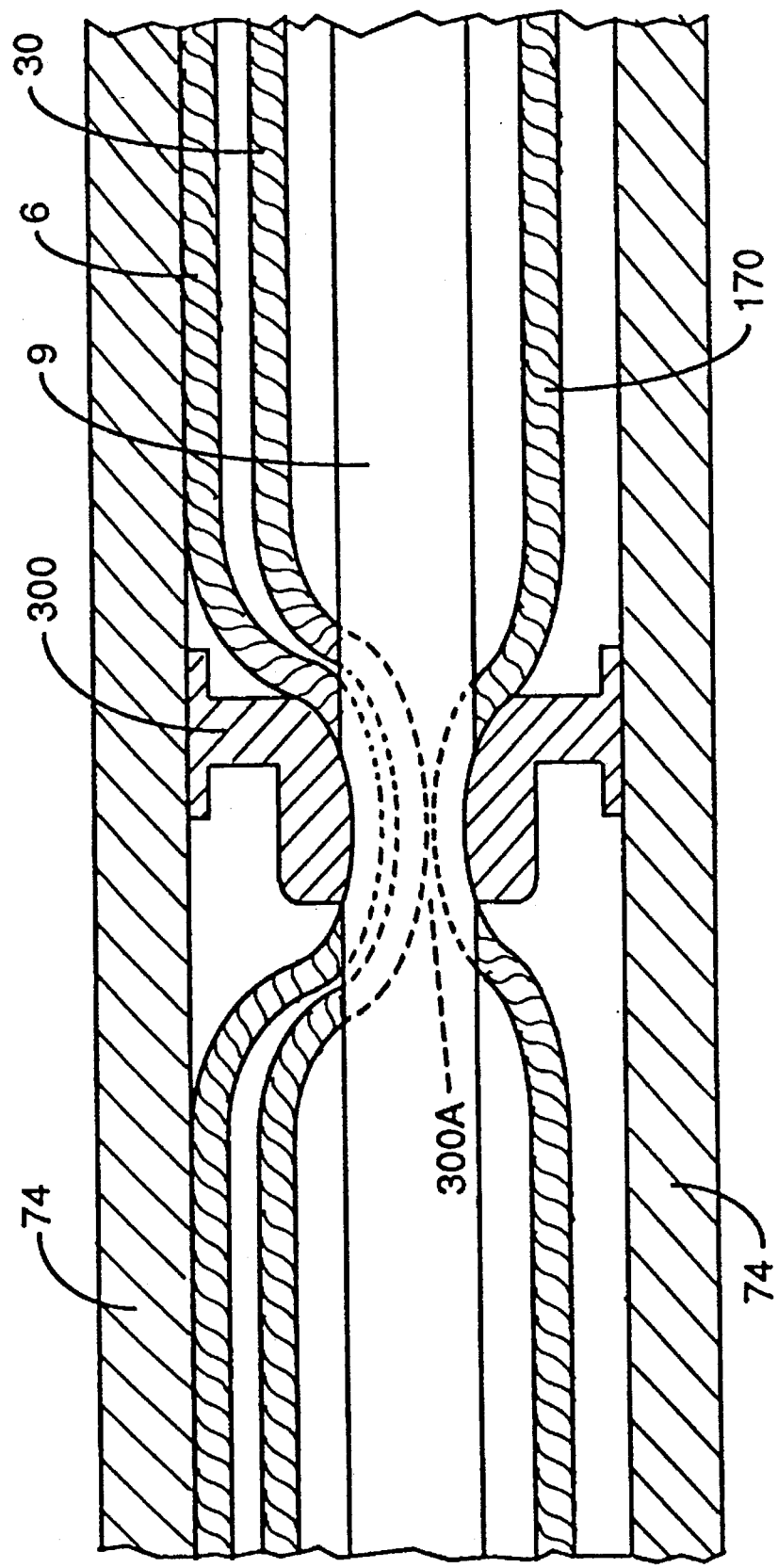
FIG. 10 is a cross sectional view of a preferred pressure seal for one preferred embodiment of the invention.

In another preferred embodiment of the invention, illustrated in FIGS. 10–12, the instrument includes a sealing device for minimizing the escape of gases from the body cavity through the shaft of the instrument to the ambient environment. This is most important in cases wherein insufflation is used to pressurize the body cavity, rendering the organs more visible to the surgeon. The seal may comprise any number of devices, including flaps, check valves, or gelatinous silicon plugs, which need not render the instrument truly airtight. The purpose of the seal is to minimize the amount of air escaping through the body cavity and the instrument while allowing the instrument to be used by allowing the cables and/or rods passing through the shaft to continue to reciprocate therein. The seal would thus allow for controlled gas escape, creating a pressure gradient involving a higher pressure on the actuator (staple head) side of the seal than on the handle assembly side. Thus, the rate of controlled gas escape will be within the pressure requirements required for the insufflation equipment to maintain the necessary pressure for adequate insufflation over the duration of the insufflation procedure.

An example of such a seal is shown in FIG. 10, wherein the seal 300 forms a sphincter within the shaft 74, the articulation belt 9 passes on the outside of the seal 300 and the various actuation cables 6, 30, 170 pass through a small hole 300A in the center of the seal 300. In another embodiment shown in FIGS. 11–12 the seal 301 has 4 flaps 301A, 301B, 301C, 301D. The seal 301 is made from an elastomeric material which permits the flaps to be flexible and bend around the cables 6, 30, 170 and the articulation belt 9. In yet another embodiment, a plug of silicone or other viscous material with relatively high surface tension, may be placed partway inside the shaft filling empty spaces between the cables and belt, providing resistance to gas flow through the shaft while still permitting relative motion of the cables and belt.

The invention in its broader aspects is not limited to the specific details of the preferred embodiments shown and described, and those of ordinary skill in the art will recognize that the invention can be practiced with modifications within the spirit and scope of the appended claims, including any and all equivalents thereof. Additionally, although certain preferred embodiments of the invention described herein satisfy one or more objects and provide one or more advantages as discussed above, is expressly contemplated that the invention may be practiced in spirit without utilizing all of the objects and advantages, and that accordingly, the objects and advantages of the invention form no part thereof, except as such may be embodied by the full scope of the following claims.

We claim:

1. A surgical instrument for applying one or more surgical fasteners to tissue, comprising:

a fastener applying assembly including fastener holding means for holding one or more surgical fasteners, means for driving said surgical fasteners into the tissue, means for capturing and clamping said tissue prior to forming said fasteners and for releasing said tissue after forming said fasteners;

a shaft assembly for mounting to the distal end thereof said fastener applying assembly;

an actuator handle assembly mounted to the proximal end of said shaft assembly and including first actuator means for actuating said means for capturing, clamping, and releasing said tissue, and further including second actuator means in cooperation with said first actuator means, said second actuator means operable to drive said surgical fasteners, wherein said first actuator means is pivotally mounted about a first pivot point to said actuator handle assembly, and said second actuator means is pivotally mounted about a second pivot point to said first actuator means, wherein said first actuator means includes clamp locking means for locking said first actuator means after said tissue is clamped.

2. The surgical instrument of claim 1 further including safety lock means for preventing actuation of said second actuator means until said first actuator means has clamped said tissue.

3. The surgical instrument of claim 2 further including actuator locking means for locking said first and second actuator means together following actuation of said first and second actuator means.

4. The surgical instrument of claim 3 further including actuator release means for releasing said first and second actuator means from locking engagement with each other.

5. The surgical instrument of claim 1 further including release button means on said actuator handle assembly for releasing said clamp locking means.

6. The surgical instrument of claim 1 wherein said fastener applying assembly includes a reloadable fastener cartridge.

7. The surgical instrument of claim 6 wherein said fastener applying assembly includes cartridge locking means for preventing said reloadable cartridge from being removed from said surgical instrument until said first and second actuator means is released from a locked position following clamping.

8. The surgical instrument of claim 1, further including seal means for maintaining a pressure gradient between the distal and proximal ends of said shaft assembly.

9. The surgical instrument of claim 1, said first actuator means further including emergency clamp release means for releasing said means for capturing and clamping said tissue from a jammed clamped position to an open position.

* * * * *